(12) United States Patent
Mori

(10) Patent No.: US 7,176,321 B2
(45) Date of Patent: Feb. 13, 2007

(54) METHOD FOR PRODUCING 3-AMINO-4-SUBSTITUTED-5-PYRAZOLONES

(75) Inventor: Hideto Mori, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 511 days.

(21) Appl. No.: 10/797,038

(22) Filed: Mar. 11, 2004

(65) Prior Publication Data

US 2004/0204589 A1 Oct. 14, 2004

(30) Foreign Application Priority Data

Mar. 14, 2003 (JP) .............................. 2003-070179

(51) Int. Cl.
*C07D 43/04* (2006.01)
(52) U.S. Cl. .............................. 548/312.1; 548/365.1; 548/366.7
(58) Field of Classification Search ............. 548/312.1, 548/365.1, 366.7
See application file for complete search history.

(56) References Cited

U.S. PATENT DOCUMENTS 4,367,282 A 1/1983 Yagihara et al.

FOREIGN PATENT DOCUMENTS

JP 62-70363 A 3/1987
JP 2002-338548 A 11/2002

OTHER PUBLICATIONS

Journal of Sysnthetic Organic Chemistry, Japan, vol. 45, No. 2, p. 151-161 Feb. 1987, Nobuo Furutachi et al.

*Primary Examiner*—Kamal A. Saeed

(74) *Attorney, Agent, or Firm*—Birch, Stewart, Kolasch & Birch, LLP

(57) ABSTRACT

The invention provides a method for producing a compound represented by the following formula (II), comprising executing alkali hydrolysis of a compound represented by the following formula (I) with an alkali metal hydroxide in the presence of a barium compound to from the compound represented by formula (II), precipitating the barium compound in the form of a barium halide, and eliminating the barium halide:

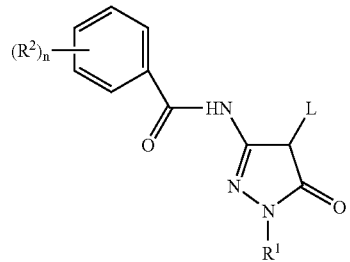

Formula (I)

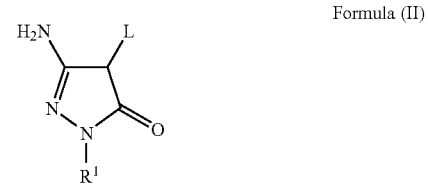

Formula (II)

wherein L represents a thiocyano group, an aryloxy group, an alkoxy group, an alkylthio group, an arylthio group, a heterocyclic thio group, an imide group, an imidazolyl group, a pyrazolyl group or a triazolyl group; $R^1$ represents an unsubstituted or substituted alkyl group, or an unsubstituted or substituted aryl group; $R^2$ represents a substituent; and n represents an integer of 0 to 5; in a case where n is 2 or larger, $R^2$ may be the same or different.

12 Claims, No Drawings

METHOD FOR PRODUCING 3-AMINO-4-SUBSTITUTED-5-PYRAZOLONES

CROSS-REFERENCE TO RELATED APPLICATION

This application claims priority under 35 U.S.C. 119 from Japanese Patent Application NO. 2003-70179, the disclosure of which is incorporated by reference herein.

BACKGROUND OF THE INVENTION

1. Field of the Invention

The present invention relates to a method for producing 3-amino-4-substituted-5-pyrazolones and more particularly to a method for producing 3-amino-4-substituted-5-pyrazolones useful as a coupler intermediate for photosensitive materials, or as an intermediate for color marking materials.

2. Description of the Related Art

A two-equivalent coupler for forming a magenta color image, which the two-equivalent coupler is a homopolymer or a copolymer including a repeating unit derived from an ethylenic unsaturated monomer including a pyrazolone residue, is particularly useful as a magenta color-forming coupler for color photography of a subtractive color system (see U.S. Pat. No. 4,367,282).

Such an ethylenic unsaturated monomer including a pyrazolone residue, providing the repeating unit of the polymer coupler, can be synthesized by a method which includes a step of introducing, in 4-position, a group releasable by a coupling reaction with the oxidant of developing agent (such a group hereinafter also called "coupling releasable group"), and which combines a residue having an ethylenic unsaturated group to an amino group in 3-position of a 3-amino-4-substituted-5-pyrazolone. The 3-amino-4-substituted-5-pyrazolone used as an intermediate has usually been synthesized, as indicated by the following reaction scheme by protecting the amino group in 3-position of a 3-amino-5-pyrazolone (A) which is a starting material with an acetyl group, halogenating 4-position of the resultant compound, introducing a coupling releasable group by substitution reaction of the halogen and removing the acetyl group (see J. of Synthetic Organic Chem. Japan, Vol. 45, No. 2, p. 151–161 (1987)).

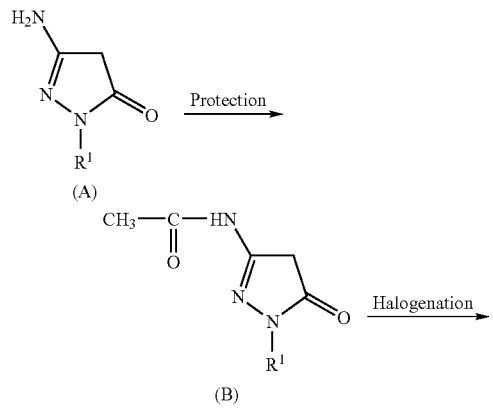

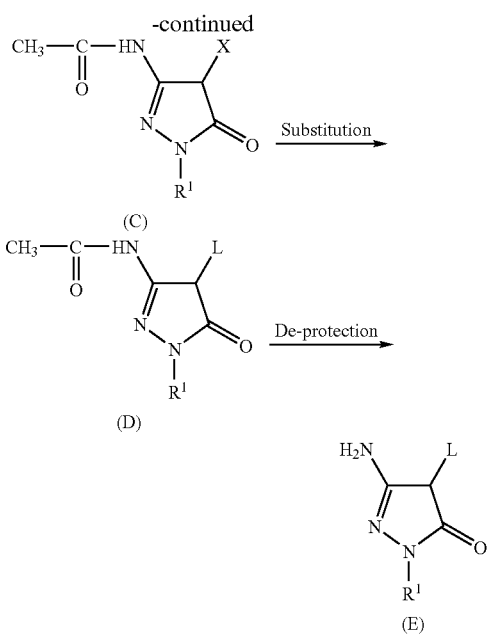

A key step in the foregoing reaction scheme is a substitution step of obtaining a compound (D) from a compound (C). This step, however, has drawbacks of a very low yield and high incidence of by-products, due to inhomogenization of 4-halogenated material, generation of carbene (separation of a halogen atom with electron pairs from the 4-halogenated material resulting in generation of carbene), and subsequent by-reactions such as imerization/trimerization. Of the carbene. In order to avoid such as drawbacks, it has been reported that use of a benzoyl group for protecting the 3-amino group significantly improves the yield of the substitution step (see JP-A No. 62-70363). In such a method, acid hydrolysis is employed for de-protection of the benzoyl group.

However, de-protection of the benzoyl group by acid hydrolysis requires a higher temperature and a longer time than de-protection of the acetyl group, which cannot avoid by-reactions such as partial cleavage of the pyrazolone ring and increase in coloring component amount. As a result, when a polymer coupler synthesized from the compound obtained in this method is applied in a photosensitive material, photographic characteristics deteriorate.

In order to avoid drawbacks resulting from such a de-protection step, a method has been reported in which de-protection of the benzoyl group of a 3-benzoylamino-4-substituted-5-pyrazolone having the benzoylamino group in 3-position is conducted by alkali hydrolysis in the presence of a specified metal compound such as a barium compound or a lithium compound and neutralization of the reaction mixture with oxalic acid (see JP-A No. 2002-338548).

However, when producing on an industrial scale, the producing method described in JP-A No. 2002-338548 is not necessarily satisfactory in manipulating properties thereof and the like, and further improvements have been desired.

More specifically, according to investigations by the present inventors, improvements are required in processing of barium compound after execution of alkali hydrolysis and in ensuring the quality of 3-amino-4-substituted-5-pyrazolones to be obtained. These improvements become important particularly in mass production.

Since processed water used in the reaction contains a large amount of barium ions, and cannot be discharged as it is from the standpoint of maintaining a clean environment, it is necessary to remove the barium ions in some manner. In the method described in JP-A No. 2002-338548, the barium compound is treated with oxalic acid, but the resulting barium oxalate is extremely poor in fluidity and filterability of the reaction liquid and is unsuitable for mass production. As a result, such a barium compound remains in the obtained 3-amino-4-substituted-5-pyrazolones, resulting in deteriorated quality such as turbidity.

Also, when a reaction mixture is colored, it is effective to remove coloring components by extracting an aqueous phase containing a desired substance with an organic solvent. For such a purpose, extraction with an aliphatic halogenated organic solvent such as 1,2-dichloroethane is effective. However, because of recent concern regarding the detrimental influence of halogenated organic substances, particularly chlorinated compounds, on the environment, usage of organic solvents has been required which does not affect the environment.

As explained in the foregoing, prior production methods have not been advantageous in productivity, separation and purification of a desired product, time required for manufacture, and consideration on the environment, and there has been a strong desire for a technology capable of producing a large amount of highly pure 3-amino-4-substituted-5-pyrazolones through simple operations.

Thus, there has been a need for a method for producing, at a high yield, a highly pure 3-amino-4-substituted-5-pyrazolone which does not cause deterioration in photographic performance due to impurities, which method can be conducted economically on an industrial scale, with the environment taken into consideration, and with waste material reduced as much as possible.

SUMMARY OF THE INVENTION

The present invention provides a method for producing a compound represented by the following formula (II), comprising executing alkali hydrolysis of a compound represented by the following formula (I) with an alkali metal hydroxide in the presence of a barium compound to from the compound represented by formula (II), precipitating the barium compound in the form of a barium halide, and eliminating the barium halide:

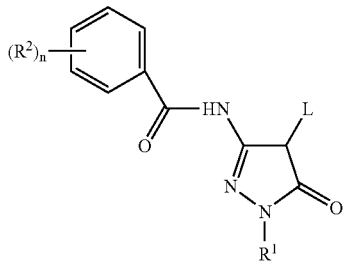

Formula (I)

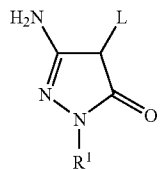

Formula (II)

In formulas (I) and (II), L represents a thiocyano group, an aryloxy group, an alkoxy group, an alkylthio group, an arylthio group, a heterocyclic thio group, an imide group, an imidazolyl group, a pyrazolyl group or a triazolyl group, and $R^1$ represents an unsubstituted or substituted alkyl group, or an unsubstituted or substituted aryl group. In formula (I), $R^2$ represents a substituent; and n represents an integer of 0 to 5. When n is 2 or larger, $R^2$ may be the same or different.

The producing method of the invention enables production of a high quality 3-amino-4-substituted-5-pyrazolone useful as an intermediate for a magenta image forming 2-equivalent coupler used in a photographic photosensitive material, or as an intermediate for a color marking material, at a high yield with superior operability in an economically advantageous manner, consideration on the environment, and reduction of waste material as much as possible.

DETAILED DESCRIPTION OF THE INVENTION

According to a method of the present invention for producing a compound represented by the following formula (II), alkali hydrolysis of a compound represented by the following formula (I) is conducted with an alkali metal hydroxide in the presence of a barium compound. After the reaction ends, the barium compound in a reaction system precipitates in the form of a halide, and the halide of the barium compound is eliminated.

At first, a detailed explanation will be given on the compounds represented by formulas (I) and (II) to be employed in the invention.

There are keto-enol tautomers in the pyrazolone ring in each of the compounds represented by formulas (I) and (II). While the chemical formulas in the present specification describe only one (keto-structure) of such tautomers to simplify explanations, needless to say, both tautomers (keto structure and enol structure) are included in the scope of the invention.

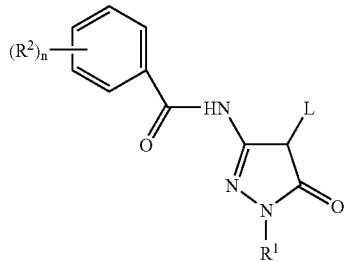

Formula (I)

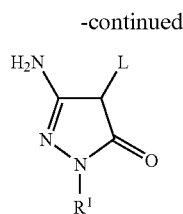

Formula (II)

In formulas (I) and (II), L represents a thiocyano group, an aryloxy group, an alkoxy group, an alkylthio group, an arylthio group, a heterocyclic thio group, an imide group, an imidazolyl group, a pyrazolyl group or a triazolyl group; and $R^1$ represents an unsubstituted or substituted alkyl group, or an unsubstituted or substituted aryl group. In formula (I), $R^2$ represents a substituent; and n represents an integer of 0 to 5. When n is 2 or larger, $R^2$s may be same or different.

Hereinafter, each group in formulas (I) and (II) will be explained.

L represents a thiocyano group, an aryloxy group (preferably an aryloxy group having 6 to 30 carbon atoms such as phenoxy or p-chlorophenoxy), an alkoxy group (such as methoxy, butoxy or decyloxy), an alkylthio group (preferably an alkylthio group having 1 to 30 carbon atoms such as methylthio, butylthio or decylthio), an arylthio group (preferably an arylthio group having 1 to 30 carbon atoms such as phenylthio), a heterocyclic thio group (preferably a heterocyclic thio group having a 3 to 10-membered ring and a hetero atom selected from a nitrogen atom, an oxygen atom and a sulfur atom; and the ring may be a monocycle or a condensed ring; or preferably a heterocyclic thio group having 0 to 30 carbon atoms such as 1-phenyl-5-tetrazolylthio or 2-benzothiazolylthio), an imide group (preferably an imide group having 4 to 30 carbon atoms such as 5,5-dimethyl-3-hydantoinyl), an imidazolyl group (preferably an imidazolyl group having 3 to 30 carbon atoms such as 1-imidazolyl), a pyrazolyl group (preferably a pyrazolyl group having 3 to 30 carbon atoms such as 1-pyrazolyl or 3,5-dimethyl-1-pyrazolyl) or a triazolyl group (preferably a triazolyl group having 2 to 30 carbon atoms such as 1-triazolyl, 1-benzotriazolyl-5,6-dimethyl-1-benzotriazolyl or 5-methoxycarbonyl-1-benzotriazolyl). When L is an alkyl group or an alkylthio group, an alkyl group or an alkylthio group with 4 to 10 carbon atoms is preferable.

These groups may be further substituted with a substituent, and examples of such a substituent include an alkyl group, an aryl group, an alkoxy group, an aryloxy group, an alkylthio group, an arylthio group, a halogen atom, a cyano group, a carboxyl group, a carbamoyl group, an acyl group, a nitro group, a substituted amino group, an alkyl- or aryl-sulfonyl group, an alkoxycarbonyl group, an aryloxycarbonyl group, and a heterocyclic group.

L can be released by coupling the compound represented by formula (I) or (II) with an oxidant of a developing agent such as an aromatic primary amine developing agent.

Among these, L is preferably an aryloxy group, an imidazolyl group, a pyrazolyl group or a triazolyl group, and more preferably a pyrazolyl group.

$R^1$ represents an unsubstituted or substituted alkyl group, or an unsubstituted or substituted aryl group. Such an alkyl group preferably has 1 to 15 carbon atoms, and may be linear, branched or cyclic (namely, a cycloalkyl group). The aryl group preferably has 6 to 30 carbon atoms, is preferably a phenyl group or a naphthyl group that may have a substituent, and particularly preferably a phenyl group that may have a substituent.

Examples of the substituent of each of the substituted alkyl group and the substituted aryl group include a halogen atom (such as fluorine atom or chlorine atom), an alkyl group (such as methyl or ethyl), an aryl group (such as phenyl or naphthyl), a cyano group, a carboxyl group, a substituted or unsubstituted carbamoyl group (such as carbamoyl, N-phenylcarbamoyl or N,N-dimethylcarbamoyl), an acyl group (such as acetyl or benzoyl), a nitro group, a substituted amino group (such as dimethylamino or anilino), a sulfonamide group (such as methanesulfonamide), an alkoxy group (such as methoxy), an aryloxy group (such as phenoxy), an alkylthio group (such as methylthio), an arylthio group (such as phenylthio), an alkylsulfonyl group (such as methylsulfonyl or hexadecanylsulfonyl), an arylsulfonyl group (such as benzenesulfonyl), and a heterocyclic group (such as morpholin-4-yl). Such a substituent group may be further substituted. When plural substituents are present, such substituents may be the same or different but preferably the same. Among these substituents, a halogen atom, a nitro group, a cyano group, a carboxyl group, an alkoxy group or an aryloxy group is preferable, and a halogen atom is more preferable, and a chlorine atom is particularly preferable. $R^1$ is particularly preferably a phenyl group substituted with 1 to 3 chlorine atoms, and more specifically a 2,5-dichlorophenyl group or a 2,4,6-trichlorophenyl group.

In formula (I), $R^2$ represents a substituent and preferable examples thereof include a halogen atom, an alkoxy group, an alkyl group, a nitro group and a cyano group. The compound represented by formula (II) is derived from, through alkali hydrolysis, the compound represented by formula (I), with a benzoic acid derivative substituted with $R^2$ liberated. Therefor it is important that such a benzoic acid derivative is easily removable from the reaction system. From such a standpoint, $R^2$ is preferably a halogen atom, an alkyl group with 1 to 4 carbon atoms, or an alkoxy group with 1 to 4 carbon atoms, and more preferably a chlorine atom, a methyl group or a methoxy group.

In formula (I), n is preferably 0, 1 or 2, more preferably 0 or 1, and particularly preferably 0.

In the following, specific examples of the compound represented by formula (I) to be employed in the invention are shown, but the invention is not limited to such examples.

Compound 1

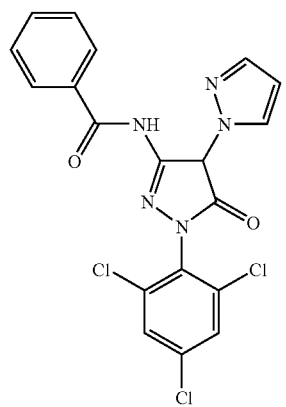

-continued
Compound 2
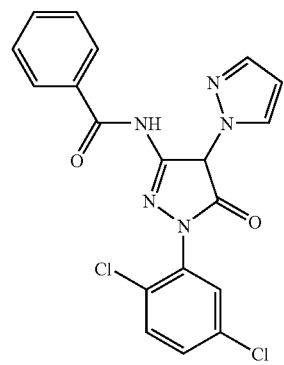
Compound 3
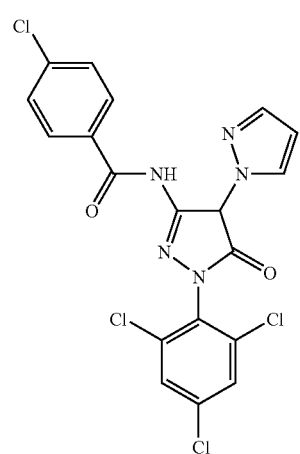
Compound 4
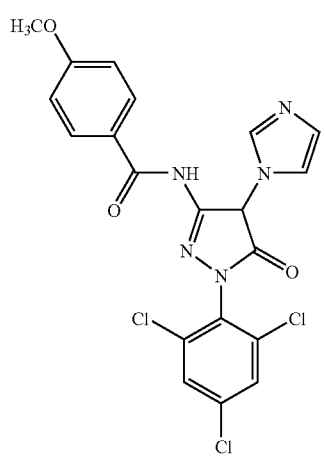
-continued
Compound 5
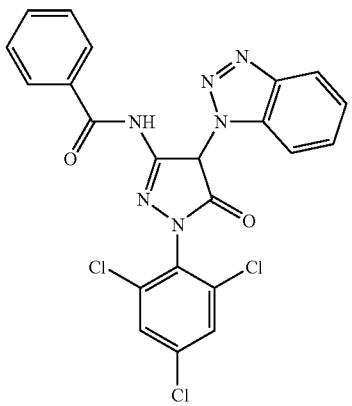
Compound 6
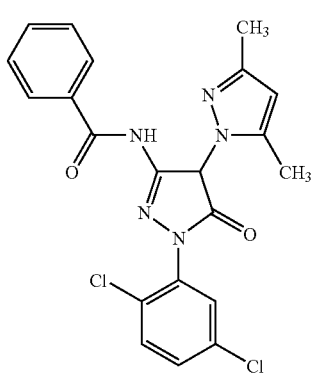
Compound 7
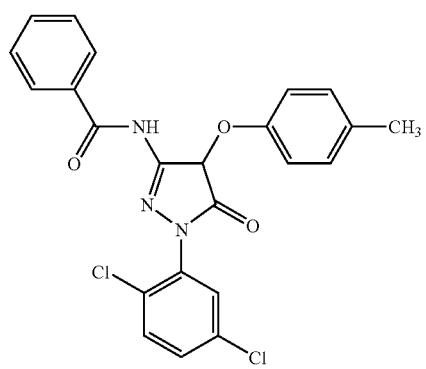
Compound 8
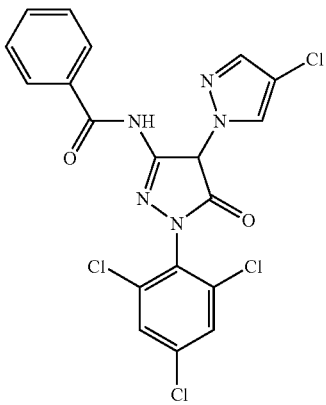

-continued

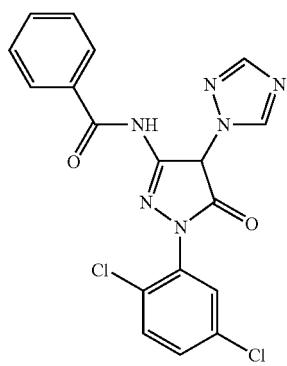

Compound 9

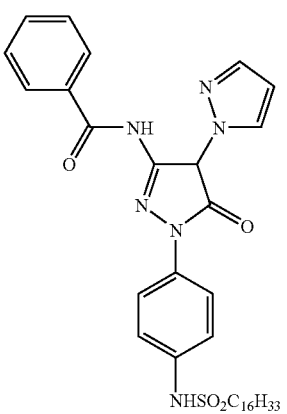

Compound 10

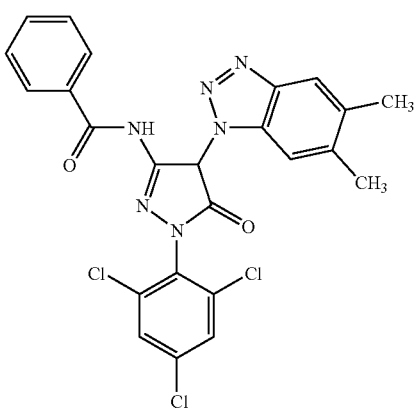

Compound 11

Specific examples of the compound represented by formula (II) can be compounds corresponding to the specific examples of the compound represented by formula (I), but the invention is not limited to such examples as explained above.

The producing method of the invention will be explained.

The compound represented by formula (I), to be employed in the invention, can be easily prepared for example by a method described in JP-A No. 62-70363. The compound represented by formula (I), prepared by such a method, may be isolated and then used for the producing method of the invention. Alternatively, the production according to the invention can follow the preparation of the compound represented by formula (I) without isolating the compound from the reaction system. The latter method is superior in reducing manufacturing cost due to, for example, a shorter production process.

A reaction solvent that can be used in a hydrolysis step of the invention is not particularly restricted as long as it does not cause operational problems such as hindered agitation by precipitation of a reaction substance, a reaction intermediate or a reaction product, and does not hinder the progress of the reaction, does not decompose during the alkali hydrolysis step of the invention and does not detrimentally affect the reaction. In consideration of halide elimination in the next step, an alcoholic solvent (such as methanol, ethanol or 2-propanol), aprotic polar solvent (such as pyrrolidones such as N-methylpyrrolidone, sulforan, imidazolidinones such as N,N-dimethylimidazolidinone, acetone, dimethylsulfoxide, acetonitrile or amides such as dimethylformamide, dimethylacetamide or hexamethylphosphotriamide), an ether solvent (such as 1,2-dimethoxyethane, tetrahydrofuran or anisole), a pyridine solvent (such as pyridine) and water can be employed. It is also possible to employ two or more solvents with a suitable mixing ratio.

Among these, an alcoholic solvent, aprotic polar solvent, pyridine or water are preferable, and methanol, 2-propanol, N-methylpyrrolidone, sulforan, and N,N-dimethylimidazolidinone are more preferable. A most preferred solvent is methanol, N-methylpyrrolidone, sulforan, water or a combination of two or three solvents selected from these.

The amount of the solvent to be employed is variable depending on the industrial scale and is not particularly restricted as long as operational problems such as hindered agitation does not occur. In view of economical efficiency and improved reactivity, the amount of the solvent is preferably 0.1 to 1000 parts by mass relative to 1 part by mass of the compound represented by formula (I), more preferably 0.5 to 100 parts by mass, and particularly preferably 1 to 10 parts by mass.

The alkali hydrolysis of the invention is executed by utilizing an alkali metal hydroxide in the presence of a barium compound. The alkali metal hydroxide can be sodium hydroxide, potassium hydroxide or cesium hydroxide, but sodium hydroxide or potassium hydroxide is preferable. The alkali metal hydroxide can be employed in the form of flakes or pellets, or a solution having an arbitrary concentration (for example, a 25% (W/V) aqueous solution of sodium hydroxide or a 48% (W/V) aqueous solution of potassium hydroxide). In consideration of production on an industrial scale, use of the alkali metal hydroxide in the form of a solution is convenient.

The amount of the alkali metal hydroxide is preferably 0.5 to 100 times as many moles as the compound represented by formula (I), more preferably 0.5 to 50 times, still more preferably 0.5 to 10 times, and particularly preferably 0.5 to 3 times.

The barium compound used in combination with the alkali metal hydroxide is preferably a compound that can be added in the form of a salt. Examples of such a barium compound include barium acetate, barium nitrate and barium hydroxide, which can also be a hydrate thereof. In the invention, barium hydroxide or a hydrate thereof is preferable.

The amount of the barium compound is preferably 0.05 to 10 times as many moles as the compound represented by formula (I). Use of an excessive amount thereof does not greatly improve the production rate or production speed of the desired product represented by formula (II), but removal of the barium compound becomes complicated later on and the amount of waste increases, thus causing problems when producing on an industrial scale. In the invention, the amount of the barium compound is more preferably 0.05 to 1 time as many moles as the compound represented by formula (I), still more preferably 0.05 to 0.5 times, and most preferably 0.05 to 0.25 times.

A reaction temperature in the hydrolysis step of the invention is preferably within a range of 20° to 200° C., more preferably 40° to 150° C., and still more preferably 50° to 90° C.

A reaction time depends on a charged amount and a reaction temperature and is usually within a range of 0.5 to 20 hours, and preferably 3 to 10 hours.

The hydrolysis step does not require an inert atmosphere, but may be executed under a flow of argon or nitrogen.

A post-processing of a reaction mixture after completion of the alkali hydrolysis reaction is executed by neutralizing or acidifying the reaction mixture with a hydrohalogenic acid. The pH of the reaction mixture after the neutralization or acidification is preferably equal to or less than 2.0. This operation causes the barium compound to precipitate as a halide, and the halide is then removed. The removal is preferably executed by a solid-liquid separation. The barium halide is a non-sticky powdered substance, and can sufficiently ensure fluidity of the post-processed reaction mixture, resulting in easy filteration at the time of the solid-liquid separation. The hydrohalogenic acid preferably employed in the invention can be hydrochloric acid, hydrobromic acid, hydroiodic acid and hydrofluoric acid, among which hydrochloric acid and hydrobromic acid are preferable and hydrochloric acid is the most preferable.

The amount of hydrohalogenic acid is preferably 2 to 50 times as many moles as the alkali employed in the alkali hydrolysis step, more preferably 2 to 20 times, and even more preferably 3 to 10 times.

Instead of hydrohalogenic acid, it is also possible to employ another acid such as sulfuric acid or oxalic acid to neutralize or acidify the reaction mixture and to thereby precipitate barium sulfate or barium oxalate, but such a method is unsuitable for mass production on an industrial scale because of fluidity of the post-processed reaction mixture and the filtering property of the precipitate are extremely poor.

Thereafter, it is preferable to have the reaction mixture, after the solid-liquid separation of the barium halide, undergo an extraction process in an acidic state with an organic solvent. Since the desired compound represented by formula (II) is soluble in an acidic aqueous solution, such an operation allows effective extraction and elimination of benzoic acid derivatives generated in the hydrolysis step, by-products contained with the used compound represented by formula (I) (by-products generated during preparation of the compound represented by formula (I), particularly those generated during the step of introducing the aforementioned substituent L), and colored components. In such an extraction process, any organic solvent separable from water can be employed, but for environmental considerations, an organic solvent not containing a halogen atom is preferable. Examples thereof include an ether solvent (such as diethyl ether, diisopropyl ether, methyl t-butyl ether, methoxybenzene or ethoxybenzene), an ester solvent (such as ethyl acetate, or n-butyl acetate), an aliphatic hydrocarbon solvent (such as hexane, or heptane) and an aromatic hydrocarbon solvent (such as toluene). In consideration of an adaptability to mass production on an industrial scale and availability/ease of recovery and re-use, an aromatic hydrocarbon solvent is preferable. Examples of the preferable aromatic hydrocarbon solvent include toluene, xylene (o-xylene, m-xylene, p-xylene or an arbitrary mixture thereof), mesitylene, ethylbenzene, t-butylbenzene, and isopropylbenzene (cumene). Among these, toluene, xylene, mesitylene and ethylbenzene are preferable and toluene and xylene are more preferable.

In the invention, it is preferable to neutralize the aqueous phase thus obtained by the extraction and to thereby precipitate the desired compound represented by formula (I) as crystals. A base to be employed in the neutralization can be, for example, a hydroxide, a carbonate salt, a hydrogencarbonate salt or an alkoxide of an alkali metal, or an amine (such as triethylamine or N-methylmorpholine), but the hydroxide of the alkali metal is particularly preferable in consideration of adaptability to mass production on an industrial scale, availability and cost.

The base can be employed in the form of flakes or pellets, or a solution having an arbitrary concentration (for example a 25% (W/V) aqueous solution of sodium hydroxide or a 48% (W/V) aqueous solution of potassium hydroxide), but, in consideration of production on an industrial scale, use of the base in the form of a solution is convenient.

The pH value of the neutralization of the aqueous phase after the extraction, for crystallizing out, depends on the structure of a desired product, but is usually preferably between 2.5 to 7.0. The crystallized compound represented by formula (II) can be easily isolated by a solid-liquid separation.

As specific representative example of the producing method of the invention, barium hydroxide and a 25% (W/V) aqueous solution of sodium hydroxide are added to a methanol suspension of 3-benzoylamino-4-(1-pyrazolyl)-1-(2,4,6-trichlorophenyl)-5-pyrazolone, and the reaction mixture is agitated at about 70° C. After the raw material is consumed, an excessive amount of concentrated hydrochloric acid is added to the reaction system, and the resulting barium chloride precipitate is eliminated by filtration, and the filtrate is extracted twice with toluene, and the aqueous phase is neutralized with a 25% (W/V) aqueous solution of sodium hydroxide to adjust the pH value of the system to 3.5. Resulting crystals are separated by filtration, washed and dried. Thus, a desired 3-amino-4-(1-pyrazolyl)-1-(2,4,6-trichlorophenyl)-5-pyrazolone is isolated.

The compound represented by formula (II), obtained in this manner, is so pure that it can usually be used in a next step without any further purification.

When the compound of the invention represented by formula (II) is used in the formation of a 2-equivalent coupler for forming a magenta dye in a photographic photosensitive material, it is possible to convert the compound by a known method, for example by a method described in JP-A No. 58-224352, to an ethylenic unsaturated monomer including a pyrazolone residue, from which a magenta dye forming 2-equivalent coupler that is a homopolymer or a copolymer including a repeating unit derived from such a monomer can be obtained.

EXAMPLES

In the following, the invention will be further explained by way of examples, but the invention is not limited by such examples.

Example 1

194 g of 3-benzoylamino-4-(1-pyrazolyl)-1-(2,4,6-trichlorophenyl)-5-pyrazolone were mixed with 400 mL of methanol, and 30 g of barium hydroxide octahydrate and 140 g of a 25% (W/V) aqueous solution of sodium hydroxide were added to the resultant mixture. After agitation of the resultant reaction mixture for 6 hours at an internal temperature of 65° C., the residual ratio of the raw material was 0.5% or less in an HPLC analysis. After the reaction mixture was cooled to 45° C., 500 mL of concentrated hydrochloric acid were added to the reaction mixture, and precipitated insoluble substances (barium chloride and sodium chloride) were eliminated by filtration. The filtrate was extracted twice with toluene, and the aqueous phase after the extraction was neutralized by adding a 25% (W/V) aqueous solution of sodium hydroxide so that the pH value of the aqueous phase became 3.5. Precipitated crystals were separated by filtration, and the obtained crystals were washed and dried to obtain 105 g of desired 3-amino-4-(1-pyrazolyl)-1-(2,4,6-trichlorophenyl)-5-pyrazolone (yield of 70.5%) as gray-white powder. The structure of the product was confirmed by $^1$H-NMR. Results of physical analyses are as follows.

<$^1$H-NMR (300 MHz: solvent CDCl$_3$, internal standard: TMS)>

δppm: 6.40 (t, 1H), 6.80 (s, 2H), 7.62 (d, 1H), 7.85 (s, 2H), 8.10 (d, 1H), 10.15 (s, 1H)

<HPLC> column: YMC-AM-302, 4.6 mm×150 mm eluent: a mixture of methanol, water, acetic acid, and triethylamine at a volume ratio of 1200/800/4/4, flow rate 1 mL/min detection wavelength: 254 nm Purity was 99.7% according to an HPLC relative area method (%) under the above-mentioned conditions.

<Turbidity>

Turbidity of a solution in which 0.5 g of the obtained gray-white powder was dissolved in 50 mL of methanol was measured with a turbidity meter and was 0.1 ppm or less.

<Visible Absorption Value>

The visible absorption value of the above-mentioned solution used for turbidity measurement was measured with a spectrophotometer.

| liquid thickness: | 10 mm |
| reference: | methanol |
| measurement wavelength: | 380 and 480 nm |

Under the above conditions, visible absorption values at 380 nm and 480 nm were 0.050 and 0.010, respectively.

Example 2

Example of a Continuous Process from Preparation of a Compound Represented by Formula (I) to Preparation of a Compound Represented by Formula (II)

200 g of 3-benzoylamino-4-bromo-1-(2,4,6-trichlorophenyl)-5- pyrazolone, 59 g of pyrazol, 14 g of 2,6-di-t-butyl-p-cresol and 100 mL of N-methylpyrrolidone were mixed, and the resultant reaction mixture was heated at 75° C. under a nitrogen gas flow while agitated. The reaction mixture was cooled to 45° C., and 400 mL of methanol, 25 g of barium hydroxide octahydrate and 138 g of a 25% (W/V) aqueous solution of sodium hydroxide were added to the reaction mixture. The resultant mixture was agitated for six hours at an internal temperature of 65° C. After the reaction mixture was cooled to 45° C., 500 mL of concentrated hydrochloric acid were added to the mixture, and precipitated insoluble substances (barium chloride and sodium chloride) were eliminated by filtration. The filtrate was extracted twice with toluene, and the aqueous phase after the extraction was neutralized by adding a 25% (W/V) aqueous solution of sodium hydroxide so that the pH value of the aqueous phase became 3.5. Precipitated crystals were separated by filtration, and the obtained crystals were washed and dried to obtain 109 g of desired 3-amino-4-(1-pyrazolyl)-1-(2,4,6-trichlorophenyl)-5-pyrazolone (yield: 73.3%) as gray-white powder.

Results of physical analyses (under same measuring conditions as in Example 1) are as follows:

| purity by HPLC: | 99.8% |
| | (% by relative area method) |
| turbidity: | 0.1 ppm or less |
| visible absorption values: | 0.056 (380 nm) |
| | 0.009 (480 nm). |

Comparative Example 1

Case in which Neutralization After Alkali Hydrolysis was Conducted with Oxalic Acid A compound having a1-pyrazolyl group at 4-position was synthesized from 200 g of 3-benzoylamino-4-bromo-1-(2,4,6-trichlorophenyl)-5-pyrazolone, 59 g of pyrazol, 14 g of 2,6-di-t-butyl-p-cresol, and 100 mL of N-methylpyrrolidone in a the same manner as in Example 2. This intermediate was subjected, without isolation, to a hydrolysis step with 400 mL of methanol, 25 g of barium hydroxide octahydrate, and 138 g of a 25% (W/V) aqueous solution of sodium hydroxide in the same manner as in Example 2. Neutralization of the reaction liquid after the reaction was conducted with oxalic anhydride, which was added in divided portions. In this operation, oxalic anhydride was employed in such an amount as to obtain the same pH value as that of the reaction mixture after neutralization with concentrated hydrochloric acid as in Example 2. Since barium oxalate precipitated in this operation, the neutralized reaction mixture had extremely poor fluidity, and could not be taken from the flask used. Also in the filtration of barium oxalate, operating property and filtering property were so poor that subsequent operations could not be executed.

Comparative Example 2

Case in which Neutralization After Alkali Hydrolysis was Conducted with Sulfuric Acid Neutralization was conducted in the same manner as in Comparative Example 1 except that neutralization after the alkali hydrolysis reaction was executed with concentrated sulfuric acid. Since barium sulfate precipitated in this operation, the neutralized reaction mixture had extremely poor fluidity, as in the case of neutralization with oxalic acid, and subsequent operations could not be executed.

Comparative Example 3

Elimination of Benzoyl Protective Group by Acid Hydrolysis 100 g of 3-benzoylamino-4-(1-pyrazolyl)-1-(2,4,6-trichlorophenyl)-5-pyrazolone were mixed with 350 mL of ethanol and 200 mL of concentrated hydrochloric acid, and the resultant reaction mixture was heated and refluxed for 6 hours. The raw material dissolved with progress of the reaction, reddish brown oil adhered to the flask wall, and the reaction liquid turned red. After heating and refluxing for 6 hours, the residual ratio of the raw material measured by HPLC was 0.1% or less, but generation of a low-polar impurity (about 15% in an HPLC relative area method) was observed, which is not generated at all under the conditions of alkali hydrolysis of the invention, employing an alkali metal hydroxide in the presence of a barium compound. After the reaction mixture was cooled to 40° C., extraction with toluene was conducted twice, and the aqueous phase was neutralized by adding a 25% (W/V) aqueous solution of sodium hydroxide so that the pH value of the aqueous phase became 3.5, and then brown crystals precipitated. The crystals were separated by filtration, washed and dried to obtain 31 g of brown powder. If it is assumed that all of the 31 g of the product were the desired 3-amino-4-(1-pyrazolyl)-1-(2,4,6-trichlorophenyll)-5-pyrazolone, then the calculated yield would be 40.7%. However, result of $^1$H-NMR and HPLC suggested a considerable amount of impurities.

Results of physical analyses (under the same measuring conditions as in Example 1) are as follows:

| | |
|---|---|
| purity by HPLC: | 81.2% |
| | (% by relative area method) |
| turbidity: | 10.3 ppm or more |
| visible absorptions values: | 0.500 or higher (380 nm) |
| | 0.100 or higher (480 nm). |

As is apparent from foregoing Examples and Comparative Examples, the producing method of the invention is superior in yield and quality of the object product and operational efficiency, and enables simple and economically advantageous manufacture.

What is claimed is:

1. A method for producing a compound represented by the following formula (II), comprising executing alkali hydrolysis of a compound represented by the following formula (I) with an alkali metal hydroxide in the presence of a barium compound to from the compound represented by formula (II), precipitating the barium compound in the form of a barium halide, and eliminating the barium halide:

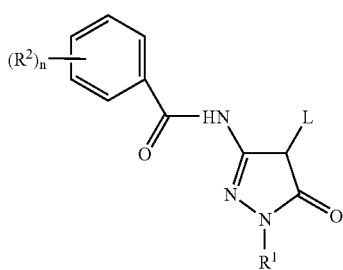

Formula (I)

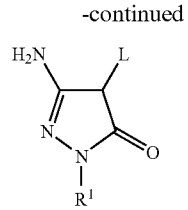

Formula (II)

wherein L represents a thiocyano group, an aryloxy group, an alkoxy group, an alkylthio group, an arylthio group, a heterocyclic thio group, an imide group, an imidazolyl group, a pyrazolyl group or a triazolyl group; $R^1$ represents an unsubstituted or substituted alkyl group, or an unsubstituted or substituted aryl group; $R^2$ represents a substituent; and n represents an integer of 0 to 5; in a case where n is 2 or larger, $R^2$ may be the same or different.

2. A method according to claim 1, further comprising, after the elimination of said barium halide, conducting addition of an organic solvent to a reaction mixture including the compound represented by formula (II) which is an aqueous phase and removal of the resultant organic phase to eliminate by-products from the aqueous phase, and neutralizing the aqueous phase after the addition and removal to precipitate the compound represented by formula (II).

3. A method according to claim 2, wherein said organic solvent for eliminating by-products does not include a halogen atom.

4. A method according to claim 3, wherein said organic solvent is an aromatic hydrocarbon organic solvent.

5. A method according to claim 1, further comprising, after said alkali hydrolysis, neutralizing a reaction mixture with a hydrohalogenic acid to precipitate the barium halide.

6. A method according to claim 2, further comprising, after said alkali hydrolysis, neutralizing a reaction mixture with a hydrohalogenic acid to precipitate the barium halide.

7. A method according to claim 3, further comprising, after said alkali hydrolysis, neutralizing a reaction mixture with a hydrohalogenic acid to precipitate the barium halide.

8. A method according to claim 4, further comprising, after said alkali hydrolysis, neutralizing a reaction mixture with a hydrohalogenic acid to precipitate the barium halide.

9. A method according to claim 5, wherein said hydrohalogenic acid is hydrochloric acid.

10. A method according to claim 6, wherein said hydrohalogenic acid is hydrochloric acid.

11. A method according to claim 7, wherein said hydrohalogenic acid is hydrochloric acid.

12. A method according to claim 8, wherein said hydrohalogenic acid is hydrochloric acid.

* * * * *